United States Patent [19]

Chandrakumar et al.

[11] Patent Number: 5,354,746
[45] Date of Patent: Oct. 11, 1994

[54] SQUARIC ACID DERIVATIVES OF SUBSTITUTED DIBENZOXAZEPINE COMPOUNDS, PHARMACEUTICAL COMPOSITIONS AND METHODS OF USE

[75] Inventors: Nizal S. Chandrakumar, Vernon Hills; Barnett S. Pitzele, Skokie, both of Ill.

[73] Assignee: G. D. Searle & Co., Chicago, Ill.

[21] Appl. No.: 69,503

[22] Filed: Jun. 1, 1993

[51] Int. Cl.$^5$ .................. C07D 267/20; C07D 281/16; C07D 413/08; A61K 31/55
[52] U.S. Cl. ..................................... 514/211; 540/547
[58] Field of Search .................... 540/547; 514/211

[56] References Cited

U.S. PATENT DOCUMENTS

| 2,852,528 | 9/1958 | Hoffmann | 260/327 |
| 3,210,372 | 10/1965 | Harvey | 260/309.6 |
| 3,357,998 | 12/1987 | Cusic | 260/333 |
| 3,534,019 | 10/1970 | Coyne | 260/239 |
| 3,624,104 | 11/1971 | Cusic | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244 |
| 4,170,593 | 10/1979 | Mueller | 260/243.3 |
| 4,290,953 | 9/1981 | Koizumi | 260/333 |
| 4,379,150 | 4/1983 | Ito | 424/244 |
| 4,559,336 | 12/1985 | Mueller | 514/211 |
| 4,559,337 | 12/1985 | Mueller | 514/211 |

(List continued on next page.)

FOREIGN PATENT DOCUMENTS

| 0012385 | 6/1980 | European Pat. Off. . |
| 0193822 | 9/1986 | European Pat. Off. . |
| 0218077 | 4/1987 | European Pat. Off. . |
| 0480641A1 | 4/1992 | European Pat. Off. . |
| 0534667 | 3/1993 | European Pat. Off. . |
| 6700603 | 7/1967 | Netherlands . |

(List continued on next page.)

OTHER PUBLICATIONS

Pat. application Ser. No. 07/813,316 filed Dec. 20, 1991 by Hagen.
Pat. application Ser. No. 08/021,694 filed Feb. 24, 1993 by Dappen.
Pat. application Ser. No. 08/056,704 filed Apr. 30, 1993 by Chandrakumar.
A. Bennett, et al. "Antagonism of Prostanoid-Induced Contractions of Rat Gastric Fundus Muscle by SC-19220 Sodium Meclofenamate, Indomethacin or (List continued on next page.)

*Primary Examiner*—Cecilia Tsang
*Assistant Examiner*—P. I. Datlow
*Attorney, Agent, or Firm*—Roberta L. Hastreiter; Roger A. Williams

[57] ABSTRACT

The present invention provides substituted dibenzoxazepine compounds of Formula I:

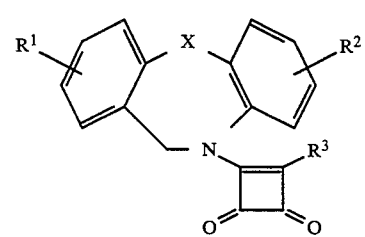

Formula I which are useful as analgesic agents for the treatment of pain, and as prostaglandin-$E_2$ antagonists for the treatment of prostaglandin-$E_2$ mediated diseases, pharmaceutical compositions comprising a therapeutically-effective amount of a compound of Formula I in combination with a pharmaceutically-acceptable carrier, a method for eliminating or ameliorating pain in an animal, and a method for treating prostaglandin-$E_2$ mediated diseases in an animal, comprising administering a therapeutically-effective amount of a compound of Formula I to the animal.

17 Claims, No Drawings

U.S. PATENT DOCUMENTS

| | | | |
|---|---|---|---|
| 4,614,617 | 9/1986 | Mueller | 540/547 |
| 4,681,939 | 7/1987 | Mueller | 540/547 |
| 4,704,386 | 11/1987 | Mueller | 514/211 |
| 5,180,720 | 1/1993 | Husa | 514/211 |
| 5,182,272 | 1/1993 | Halunan | 514/80 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |
| 5,304,644 | 4/1994 | Husa et al. | 540/547 |

FOREIGN PATENT DOCUMENTS

| | | |
|---|---|---|
| WO92/19617 | 11/1992 | PCT Int'l Appl. . |
| WO93/07132 | 4/1993 | PCT Int'l Appl. . |
| WO93/09104 | 5/1993 | PCT Int'l Appl. . |
| 1170322 | 4/1969 | United Kingdom . |
| 1331892 | 9/1973 | United Kingdom . |
| 1522003 | 8/1978 | United Kingdom . |

OTHER PUBLICATIONS

Trimethoquinol," *Br. J. Pharmac.*, 71, 169–175 (1980)--London.

W. E. Coyne, et al. "Anticonvulsant Semicarbazides," *J. Med. Chem.*, 11(6), 1158–1160 (1968)-USA.

E. J. Drower, et al. "The Antiociceptive Effects of Prostaglandin Antagonists in the Rat," *European Journal of Pharmacology*, 133, 249–256 (1987)-Europe.

F. R. George, et al. "Antagonism of Alcohol Hypnosis by Blockade of Prostaglandin Synthesis and Activity: Genotype and Time Course Effects," *Pharmacology, Biochemistry & Behavior*, vol. 19, 131–136 (1983)-USA.

R. Gimet, et al. "Quantitative Determination of Polymorphic Forms in a Formulation Matrix Using the Near Infra-Red Reflectance Analysis Technique," *Journal of Pharmaceutical & Biomedical Analysis*, vol. 5, No. 3, 205–211 (1987)-Great Britain.

A. Gomes, et al. "Pharmacodynamics of Venom of the Centipede *Scolopendra Subspinipes Dehaani,*" *Indian Journal of Experimental Biology*, vol. 20, 615–618, Aug. (1982)-India.

K. Gyrires, et al. "The Use of the Writhing Test in Mice for Screening Different Types of Analgesics," *Arch. Int. Pharmacodyn*, 267, 131–140 (1984)-USA.

D. E. MacIntyre, et al. "Antagonism of Human Platelet Responses to Stimulatory and Inhibitory Prostaglandins," *Prog. Lipid. res.*, 20(1-4), 453–9 (1981)-USA.

C. A. Maggi, et al. "The Effect of SC-19220, a Prostaglandin Antagonist, on the Micturition Reflex in Rats," *European Journal of Pharmacology*, 152, 273–279 (1988)-Europe.

K. Nagarajan, et al. "Synthesis of 10,11-Dihydrodibenz[b,f][1,4]oxazepine Derivatives as Potential Anticonvulsant & Psychotropic Agents," *Indian Journal of Chemistry*, vol. 24B, 840–844 (1985)-India.

S. Nakajyo, et al. "Inhibitory Effect of Bassianolide, a Cyclodepsipeptide, on Drug-Induced Contractions of Isolated Smooth Muscle Preparations," *Japan J. Pharmacol.*, 32, 55–64 (1982)-Japan.

A. Rakovska, et al. "Antagonistic Effect of SC-19220 on the Responses of Guinea-Pig Gastric Muscles to Prostaglandins $E_1$, $E_2$, and $F_{2a}$," *Arch. Int. Pharmacodyn.*, 268, 59–69 (1984)-USA.

J. H. Sanner "Dibenzoxazepine Hydrazides as Prostaglandin Antagonists," *Intra-Science Chem. Rept.*, vol. 6, No. 1, 1–9 (1972)-USA.

J. H. Sanner, et al. "Structure-Activity Relationships of Some Dibenzoxazepine Derivatives as Prostaglandin Antagonists," *Advances in the Biosciences*, 9, 139–148 (1972)-USA.

SQUARIC ACID DERIVATIVES OF SUBSTITUTED DIBENZOXAZEPINE COMPOUNDS, PHARMACEUTICAL COMPOSITIONS AND METHODS OF USE

BACKGROUND OF THE INVENTION (1) Field of the Invention

The present invention generally relates to compounds having pharmacological activity which are useful as pharmaceutical agents and, more particularly, as analgesic agents for the treatment of pain, and as prostaglandin-$E_2$ antagonists for the treatment of prostaglandin-$E_2$ mediated diseases, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain and prostaglandin-$E_2$ mediated diseases employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever and inflammation, such as salicylates.

Although the efficacy of opiates in relieving pain is well established, the associated addiction liability of opiates is a distinct disadvantage of these compounds.

While salicylate and salicylate-like agents (nonsteroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. No. 3,357,998 discloses derivatives of dihydrodibenz[b,f][1,4]oxazepine-10-carboxylic acids.

U.S. Pat. No. 4,170,593 discloses 1-(substituted amino)alkanoyl-2-(dibenzoxazepine-10-carbonyl) hydrazines and derivatives thereof.

U.S. Pat. No. 4,614,617 discloses intermediates for 8-chlorodibenz[b,f][1,4]oxazepine-10(11H)-carboxylic acid, 2-(sulfinyl- and sulfonyl-containing acyl)hydrazides.

U.S. Pat. No. 4,681,939 discloses 8-chlorodibenz[b,f][1,4]oxazepine-10(11H)carboxylic acid, 2-[(substituted phenylsulfinyl)alkanoyl]hydrazides and 8chlorodibenz[b,f][1,4]oxazepine-10(11H)-carboxylic acid, 2-[(substituted phenylsulfonyl)alkanoyl]-hydrazides.

U.S. Pat. No. 4,290,953 discloses dibenz[b,f][1,4]oxazepine derivatives which are stated to have serum cholesterol lowering activity, serum lipid lowering activity, blood lipid peroxide lowering activity and antiaggregation of platelet activity.

U.S. Pat. No. 3,534,019 discloses compounds which are hydrazides of tricyclic N-carboxylic acids.

U.S. Pat. No. 4,379,150 discloses dibenz[b,f][1,4]oxazepine derivatives which may have a heterocyclic ring present in the side chain at the 10-position of the molecule.

European Patent Application Publication No. 0 480 641 A1 discloses tricyclic heterocycles which are stated to have anti-hyperalgesic properties.

European Patent Application Publication No. 0 534 667 A1 discloses tricyclic heterocycles which are stated to counteract mild to moderate pain by virtue of their anti-hyperanalgesic properties.

Each of the documents described hereinabove discloses compounds which are structurally different from the compounds of the present invention. Thus, the compounds of the present invention are structurally distinct from that which has been described in the art.

SUMMARY OF THE INVENTION

The present invention provides compounds having a structure of Formula I:

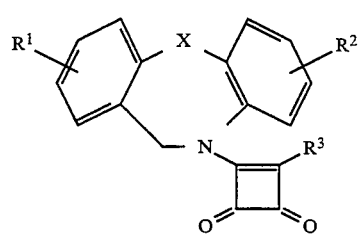

Formula I or a pharmaceutically-acceptable salt thereof, wherein:
X is oxygen, sulfur,

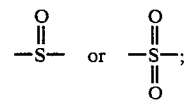

$R^1$ is hydrogen or halogen;
$R^2$ is hydrogen or halogen;
$R^3$ is —$NR^4R^5$, alkoxy,

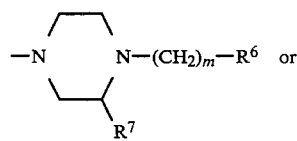

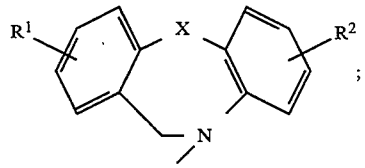

$R^4$ is hydrogen or alkyl;
$R^5$ is alkyl, alkylene-$NR^4R^4$ or alkylaryl;
$R^6$ is —$CH_3$ or aryl;
$R^7$ is hydrogen or

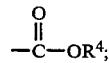

and
m is an integer of from 0 to 5.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal, or for treating a prostaglandin-$E_2$ mediated disease, comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, propyl, isopropyl, butyl, sec-butyl, isobutyl, tert-butyl, pentyl and the like.

The term "alkylene" as used herein means a straight or branched saturated hydrocarbon chain spacer arm which has from one to ten carbon atoms, and within which includes from one to six carbon atoms, and further within which includes from one to three carbon atoms.

The term "alkylaryl" as used herein means an alkylene group, as defined above, which has an aryl group, as defined below, attached thereto.

The term "alkoxy" as used herein means an alkyl radical, as defined above, having an oxygen atom attached thereto. Representative alkoxy groups include methoxy, ethoxy, propoxy, tert-butoxy and the like.

The abbreviation "AlMe$_3$" as used herein means trimethylaluminum.

The term "amino" as used herein means an -NH$_2$ group.

The term "analgesia" as used herein means the reduction, or absence, of sensibility to pain, designating particularly the relief of pain without loss of consciousness.

The term "animal" as used herein includes mammals and nonmammals, and further includes humans and nonhuman mammals.

The term "aryl" as used herein means 5- and 6-membered single-ring aromatic radicals which may include from zero to four heteroatoms, and within which includes from zero to two heteroatoms, and further within which includes from zero to one heteroatom. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "Boc" as used herein means t-butyloxycarbonyl.

The term "carbonyl" as used herein means a

group.

The term "carboxy" as used herein means a

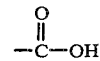

group.

The term "composition" as used herein means a product which results from the combining of more than one element or ingredient.

The abbreviation "DMAP" as used herein means 4-(dimethylamino)pyridine.

The abbreviation "DMF" as used herein means dimethylformamide.

The phrase "EC$_{50}$ concentration" as used herein means that concentration of a compound or drug which produces 50% of a maximal biological effect, such as contractions in isolated segments of guinea pig ileum.

The phrase "ED$_{50}$ dose" as used herein means that dose of a compound or drug which produced a biological effect, such as producing analgesia, in 50% of the animals to which the compound or drug was administered.

The abbreviation "DR" as used herein means dose ratio.

The abbreviation "Et" as used herein means ethyl (—CH$_2$CH$_3$).

The abbreviation "EtOAc" as used herein means ethyl acetate.

The abbreviation "EtOH" as used herein means ethanol (CH$_3$CH$_2$OH).

The abbreviation "Et$_3$N" as used herein means triethylamine.

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "$^1$H NMR" as used herein means Proton Nuclear Magnetic Resonance.

The abbreviation "HPLC" as used herein means High Pressure Liquid Chromatography.

The term "hydroxy" as used herein means the group —OH.

The term "intragastrically" and/or the abbreviation "i.g." as used herein mean that a compound or drug was administered into the stomach.

The abbreviation "i.p." as used herein means that a compound or drug was administered intraperitoneally.

The abbreviation "IR" as used herein means infrared (referring to an infrared spectrum).

The abbreviation "LAH" as used herein means lithium aluminum hydride.

The abbreviation "Me" as used herein means methyl (—CH$_3$).

The abbreviation "MeOH" as used herein means methanol (—CH$_3$OH).

The abbreviation "mp" as used herein means melting point.

The abbreviation "MPLC" as used herein means Medium Pressure Liquid Chromatography.

The abbreviation "n-BuLi" as Used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laureate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laureate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "Pr" as used herein means propyl.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the -2, 3-, -5, -7, -8 and/or 10-position is substituted.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkyl-amino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laureate, benzoate, lactate, phosphate, tosylate, citrate, maleate, fumarate, succinate, tartrate, naphthoate, mesylate, glucoheptonate, lactobionate, and laurylsulphonate salts and the like. (See, for example, S. M. Berge et al., "Pharmaceutical Salts," *J. Pharm. Sci*, 66, 1-19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are the compounds shown and described in Examples 2, 4, 5, 6 and 7 hereinbelow. The most preferred embodiment of this invention is the compound shown and described in Example 7 hereinbelow.

(3) Utility

Compounds within the present invention have been found to exhibit activity as prostaglandin $E_2$ antagonists (antagonists of prostaglandins of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating prostaglandin-$E_2$ mediated diseases, such as convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, salicaldehyde or the corresponding mercapto compound (wherein $R^1$ is hydrogen or halogen) is reacted with base and to this is added a substituted 2-chloronitrobenzene (wherein $R^2$ is hydrogen or halogen). The resulting ether or thioether is reduced to yield substituted dibenz[b,f][1,4]oxazepine or sulfur analog, wherein $R^1$ and $R^2$ are as described hereinabove, wherein X is oxygen or sulfur. In the resulting compound, $R^3$ is $-NR^4R^5$, alkoxy,

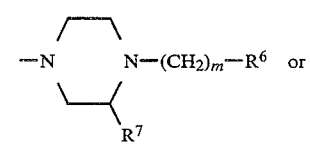

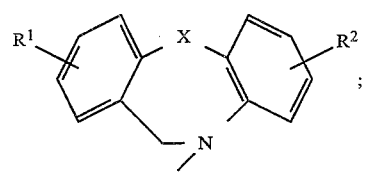

$R^4$ is hydrogen or alkyl; $R^5$ is alkyl, alkylene-$NR^4R^4$ or alkylaryl; $R^6$ is $-CH_3$ or aryl; $R^7$ is hydrogen or

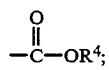

and m is an integer of from 0 to 5. Oxidation of the sulfur of the X variable is achieved with hydrogen peroxide to produce X as being

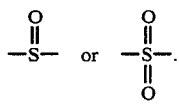

In General Reaction Scheme No. 2, a mixture of suitably protected substituted or unsubstituted dibenz[b,f][1,4]oxazepine or appropriate sulfur analog and an excess of a dialkyl squarate in solvent mixtures of diphenyl ether and dioxane is heated to reflux for several hours. Chromatography or crystallization of the crude reaction product gives dibenz[b,f][1,4]oxazepine substituted alkyl squarate (Compound-1) or the corresponding sulfur analog in addition to bis-dibenzoxazepine substituted cyclobutene-1,2-dione. Similarly, reaction of equimolar quantities of a dialkyl squarate and a substituted or unsubstituted dibenz[b,f][1,4]oxazepine gives mono substituted alkyl squarate (Compound-2). Displacement of the alkoxy group attached to the cyclobutene-dione moiety in Compound-1 is acccomplished by treating Compound-1 with a substituted or unsubstituted amine in ether solvents to provide the squaric acid derivatives. When Compound-2 is heated with substituted or unsubstituted dibenz[b,f][1,4]oxazepine in ether solvents, displacement of the alkoxy group occurs to provide the squaric acid derivatives. In General Reaction Scheme No 2, R represents alkoxy and X, $R^1$, $R^2$, $R^3$, $R^4$, $R^5$, $R^6$, $R^7$ and m are as described above in General Reaction Scheme No. 1.

GENERAL REACTION SCHEME NO. 1

A. For X = oxygen or sulfur

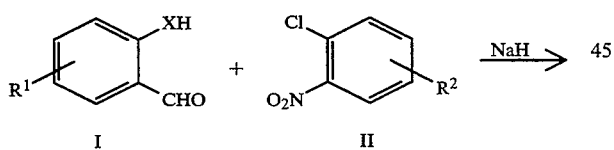

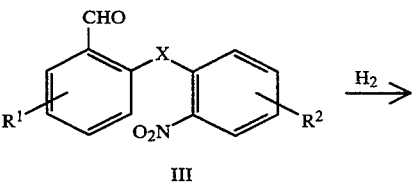

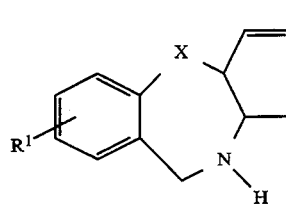

B. For X = SO or SO₂:

-continued

GENERAL REACTION SCHEME NO. 1

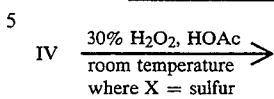

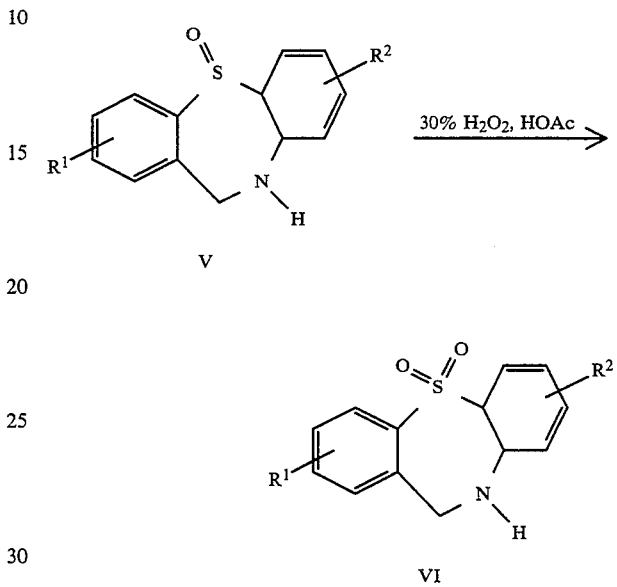

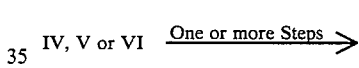

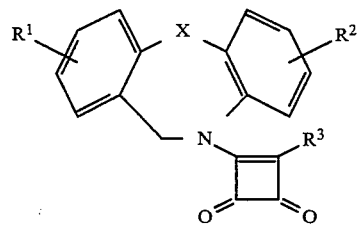

GENERAL REACTION SCHEME NO. 2

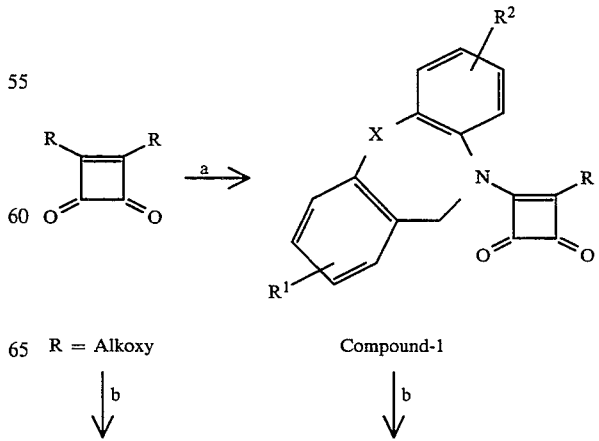

-continued
GENERAL REACTION SCHEME NO. 2

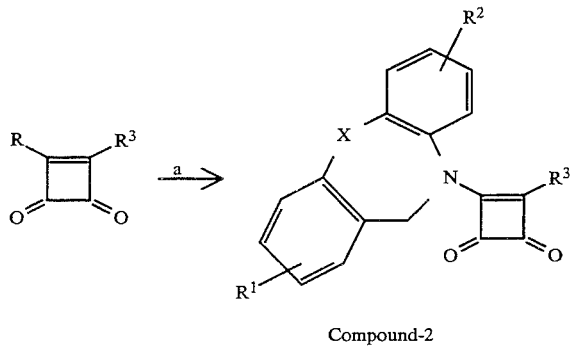

Compound-2

Key:
a. Substituted or unsubstituted dibenz[b,f][1,4]-oxazepine (0.2 weight equivalent) or equivalent sulfur analog, diphenyl ether, dioxane, 23° C. to 250° C.
b. Substituted or unsubstituted amine, diphenyl ether, ether or dioxane, 23° C. to 250° C.

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oilsoluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonitc, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

Unless indicated otherwise in a particular example, all of the starting materials, and all of the equipment, employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), TCI, American Tokyo Kasei, Inc. (Atlanta, Ga.) and Chemical Dynamics Corp. (South Plainfield, N.J.). Most of the starting materials were obtained from Aldrich Chemical Co. (Milwaukee, Wis.). The syntheses of those starting materials which are not commercially available are described in the examples presented below.

All patents and publications referred to in the examples, and throughout the specification, are hereby incorporated herein by reference, without admission that such is prior art.

EXAMPLE 1

3-Ethoxy-4-(4-ethyl-1-piperazinyl)-3-cyclobutene-1,2-dione

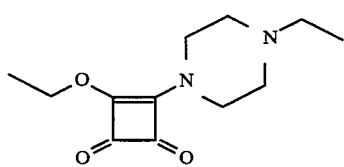

A solution of N-ethylpiperazine (1.529 g) and 3,4-diethoxy-3-cyclobutene-1,2-dione (2.29 g) in ether (40 mL) was stirred at ambient temperature for 16 hours. The precipitated solid was collected by filtration to obtain the title compound (1.5 g) as a white solid. This material was used in Example 2 without further purification.

EXAMPLE 2

3-(8-Chlorodibenz[b,f][1,4]oxazepin-10(! ! H)-yl)-4-(4-ethyl-1-piperazinyl)-3-cyclobutene-1,2-dione, monohydrochloride

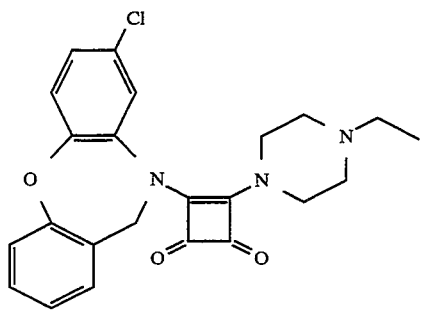

8-chloro-10,11-dihydrodibenz[b,f][1,4]oxazepine is synthesized in the manner described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz[b,f][1,4]oxazepine melting at about 94°–95° C.

A mixture of 8-chloro-dibenz[b,f][1,4]oxazepine (1.14 g) and the title product of Example 1 (1.28 g) and diphenyl ether (20 mL) was heated to reflux for 3 hours. The mixture was shaken with excess of hexane and filtered. The residue was chromatographed on silica gel using 60% ethyl acetate in hexane containing 1% each of methanol and triethylamine to obtain 0.3 g of a solid. This material was triturated with ether containing trace amount of tetrahydrofuran (THF) to obtain the free base of the title compound as a yellow solid. A sample of this material (0.1 g) was taken up in THF (3 mL) and a few drops of 6 N HCl in dioxane was added. The mixture was concentrated and the residue was triturated with acetone. The precipitated solid was filtered and dried at 78° C. (1 mm Hg) to give the title compound as a yellow solid.

Elemental Analysis data for $C_{23}H_{22}ClN_3O_3 \cdot HCl \ 0.5 \ H_2O$:

| Calculated | | Found |
|---|---|---|
| 58.86 | C | 58.95 |
| 5.15 | H | 5.06 |
| 8.95 | N | 8.90 |
| 15.11 | C | 15.13 |

EXAMPLE 3

Ethyl 4-(2-ethoxy-3,4-dioxo-1-cyclobuten-1-yl)-1-phenyl-2-piperazinecarboxylate

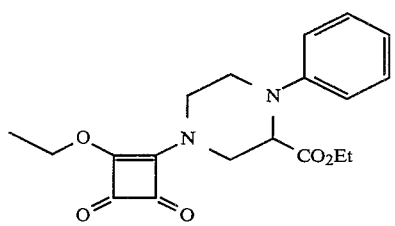

N-phenylethylenediamine (24.4 g, 0.18 mole) and benzylaldehyde (19.1 g, 0.18 mole) were mixed neat, let stand for 1 hour, diluted with Et$_2$O, and dried over NA$_2$SO$_4$. Removal of the solvent under reduced pressure gave 34.5 g of the benzaldehyde imine. To 5.0 g (22.3 mmol) of the imine dissolved in 80 mL of ethanol was added 3.0 g of NaBH$_4$ (78.9 mmol) portion-wise while stirring. After 3 hours at room temperature, all solvent was stripped under reduced pressure and the residue was dissolved in dilute HCl. This mixture was filtered, and the filtrate was made basic with dilute NaOH before extracting with Et$_2$O. This extract was dried over Na$_2$SO$_4$ and stripped of all solvent to provide 3.9 g of the desired diamine. A mixture of this diamine (31 g, 0.137 mole) and triethylamine (28 g, 0.277 mole) was added dropwise over 30 minutes to a stirred solution of ethyl-2,3-dibromopropionate (35.0 g, 0.135 mole) dissolved in 200 mL of toluene and heated to 40° C. After the addition was complete, the reaction was heated at 80°–85° C. for 7 hours, cooled to room temperature, and partitioned between water and toluene. The organic layer was separated, dried, and stripped of all solvent under reduced pressure to yield 38 g of the crude product. Chromatographic purification gave 12.8 g of ethyl 1-phenyl-4-(phenylmethyl)-2-piperazinecarboxylate. An ethanol (EtOH) (75 mL) solution of ethyl 1-phenyl-4-(phenylmethyl)-2-piperazinecarboxylate (2.20 g, 6.8 mmol) and 500 mg of 4% Pd/C was subjected to hydrogenolysis in a standard Parr apparatus. The reaction was carried out for 10 hours at 55° C. and under a hydrogen pressure of 5 psi After the catalyst was removed by filtration, and the solvent was removed by stripping under reduced pressure, 1.5 g of ethyl 1-phenyl-2-piperazinecarboxylate was obtained as a clear oil.

The procedure of Example 1 was repeated using ethyl 1-phenyl-2-piperazinecarboxylate in the place of N-ethyl piperazine to obtain the title compound as a white solid.

EXAMPLE 4

Ethyl 4-[2-(8-chlorodibenz[b,f][1,4]oxazepin-10(11H)-yl)-3,4-dioxo-1-cyclobuten-1-yl]-1-phenyl-2-piperazinecarboxylate

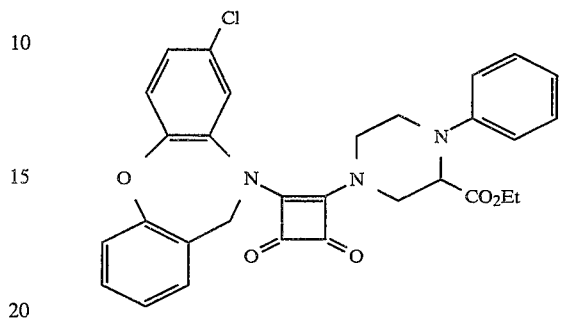

A mixture of 8-chloro-dibenz[b,f][1,4]oxazepine (1.02 g) and the product of Example 3 (0.26 g) and diphenyl ether (3 mL) was heated to reflux for 1.75 hours. The mixture was rapidly filtered thourough a small column of silica gel and the filtrate was concentrated. The residue was purified by chromatography on silica gel to obtain the title compound (0.173 g).

Elemental Analysis data for C$_{30}$H$_{20}$ClN$_3$O$_5$ . HCl. 0.5 H$_2$O:

| Calculated | | Found |
|---|---|---|
| 66.24 | C | 66.42 |
| 4.82 | H | 4.91 |
| 7.72 | N | 7.63 |
| 6.52 | Cl | 7.04 |

EXAMPLE 5

3-(8-Chloro-dibenz[b,f][1,4]oxazepin-10(11H)-yl)-4-ethoxy-3-cyclobutene-1,2-dione

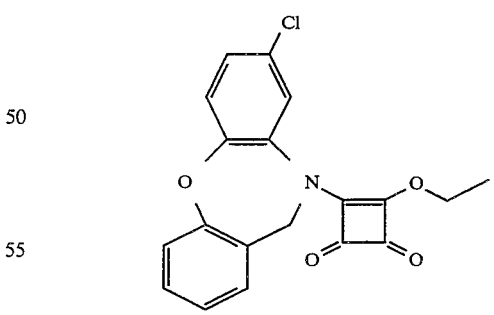

A mixture of 8-chloro-dibenz[b,f][1,4]oxazepine (2 g), 3,4-diethoxy-3-cyclobutene-1,2-dione (5 g), diphenylether (2 g) and dioxane (10 mL) was heated to reflux. After 2 hours, most of the dioxane was removed in vacuo and the precipitated title compound (0.75 g) was collected by filtration as yellow solid. The filtrate was treated with cold methanol when more of the title compound (1.2 g) precipitated. This material was used in Example 6 without further purification.

EXAMPLE 6

3-(8-Chlorodibenz[b,f][1,4]oxazepin-10(11H)-yl)-4-[[2-(dimethylamino)ethyl]amino]-3-cyclobutene-1,2-dione, hydrochloride

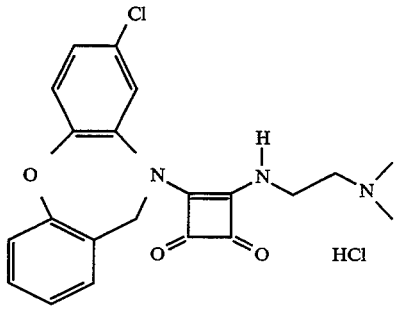

A mixture of the title product of Example 5 (0.73 g), N,N-dimethylethylenediamine (0.225 mL) and dioxane (20 mL) was heated to reflux for 20 minutes. Then, most of the dioxane was removed in vacuo and the residue was stirred in methanol (20 mL) at ambient temperature for ½ hour and the precipitated white solid was filtered and discarded. The filtrate was concentrated and the residue was chromatographed on silica gel using 1% each of methanol and triethylamine in ethyl acetate to give the free amine of the title compound as a pale yellow solid. To a solution of this solid in $CH_2Cl_2$ (3 mL) was added 7 N HCl in dioxane (1 mL) and the mixture concentrated. To the residue was added excess water and the resulting mixture was freeze dried to give the title compound.

Elemental Analysis data for $C_{21}H_{20}ClN_3O_3$. 0.9 HCl. 1.25 $H_2O$:

| Calculated | | Found |
|---|---|---|
| 55.26 | C | 55.75 |
| 4.76 | H | 5.20 |
| 9.27 | N | 8.52 |
| 14.86 | C | 14.90 |

EXAMPLE 7

3-(8-Chlorodibenz[b,f][1,4]oxazepin-10(11H)-yl)-4-[(4-pyridinylmethyl)amino]-3-cyclobutene-1,2-dione, hydrochloride

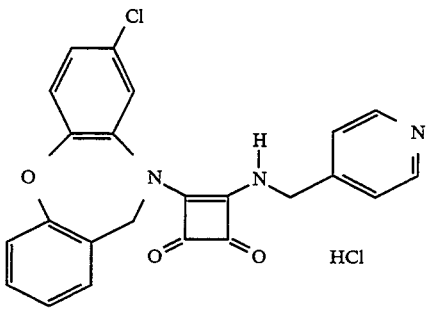

A mixture of the product of Example 5 (0.75 g), 4-(aminomethyl)pyridine (0.14 mL) and diphenylether (2 mL) was heated to reflux for 3 hours. The mixture was cooled and added to hexane (200 mL) and the separated thick oil was recovered by decantation. The oil was triturated with methanol. The precipitated solid was filtered and stirred with methanol at ambient temperature for 16 hours. The solid was then filtered and dissolved in $CHCl_3$ (4 mL). To the solution was added 7 N HCl (1 mL) and the mixture was concentrated in vacuo. The residue was triturated with ether and filtered to obtain the title compound as a yellow solid.

Elemental Analysis data for $C_{23}H_{16}ClN_3O_3$. 0.9 HCl. 0.9 $H_2O$:

| Calculated | | Found |
|---|---|---|
| 59.17 | C | 59.35 |
| 4.04 | H | 3.66 |
| 9.00 | N | 8.91 |
| 14.43 | C | 14.18 |

EXAMPLE 8

3,4-bis[8-chlorodibenz[b,f][1,4]oxazepin-10(11H)-yl]-3-cyclobutene-1,2-dione

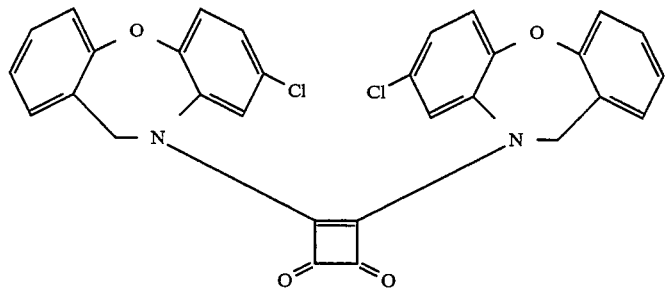

A mixture of 8-chloro-dibenz[b,f][1,4]oxazepine (2 g, 8.63 mmol), 3,4-diethoxy-3-cyclobutene-1,2-dione (0.73 g, 4.31 mmol), and diphenyl ether (5 mL) was brought to reflux for 15 minutes. The reaction mixture was cooled to room temperature, and the resulting solid was collected by filtration, and triturated on the glass fritted filter with hexane-diethyl ether. The solid was then washed with more ether, dried, and recrystallized from dichloromethane-methanol. The product was dried in a vacuum oven at 35° C. in a $N_2$ stream, and then in an Abderhalden apparatus at 110° for 18 hours with an oil pump vacuum, giving the title compound.

NMR (CDCl$_3$, 400 MHz) methylene singlet at $\delta = 5.51$, complex aromatic multiplet at $\delta$ 7.00 to 7.41. IR (CHCl$_3$, in cm$^{-1}$) 1582 (strong), 1615 (very strong), 1710 (weak), 1790 (very weak). UV-VIS (MeOH) $\lambda_x$ 393 nm, weak $\lambda_x$ at 276 rim.

Elemental Analysis data for $C_{30}H_{18}N_2O_4Cl_2 \cdot 0.25H_2O$:

| Calculated | | Found |
|---|---|---|
| 66.01 | C | 65.88 |
| 3.42 | H | 3.53 |
| 5.13 | N | 4.93 |
| 12.99 | Cl | 12.60 |

The foregoing examples are provided to enable one of ordinary skill in the art to practice the present invention. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn,* 267, 131-140 (1984); C. Vander Wende et al., *Fed. Proc.,* 15, 494 (1956); Koster et al., *Fed. Proc.,* 18, 412 (1959); and Witken et al., *J. Pharmacol. exp. Ther.,* 133, 400-408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 hereinbelow.

Charles River male albino mice, weighing 20 to 30 grams, were used in this assay.

Thirty minutes after intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," Advances in Biochemical Psychopharmacology, 8, 191 (1974).

The results for the particular compounds of the present invention analyzed in this assay, and discussed in the examples identified below which correspond thereto, are presented in Table 1 hereinbelow as fractions under the heading "WRITHING ASSAY." The fractions indicate the number of mice out of ten in which a test compound produced analgesia.

The standard initial screening dose of a test compound employed in this assay was 30 mpk per gram of body weight. If this initial screening dose of the test compound produced analgesia in seven out of ten mice, then the effect of additional doses of the test compound on the writhing response was evaluated, and then the ED$_{50}$ dose was generally calculated. (The slopes of the dose-response curves for all test compounds analyzed were compared as described by Tallarida and Murray, *Manual of Pharmacologic Calculations,* Page 11 (Springer Verlag, New York, 1981)).

All ED$_{50}$ doses calculated are also presented in Table 1 hereinbelow under the heading "WRITHING ASSAY," but as whole numbers.

(b) Prostaglandin (PGE) Antagonism Assay

In order to determine the effectiveness of several of the compounds of the present invention ("test compounds") as prostaglandin E$_2$ antagonists, a prostaglandin antagonism assay was conducted, as described below, to determine the ability of these compounds to inhibit prostaglandin E$_2$-induced contractions of segments of guinea pig ileum. If a test compound inhibits prostaglandin E$_2$-induced contractions, it suggests that the compound functionally antagonizes prostaglandin E$_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37° C. and aerated with a gaseous mixture of 95% oxygen and 5% carbon dioxide. Data for a control prostaglandin E$_2$ dose response curve plotting concentration of prostaglandin E$_2$ versus the intensity of contractions, detected isotonically, was then obtained by experimentally adjusting the dose of the prostaglandin E$_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin E$_2$ dose response curve was then generated for prostaglandin E$_2$ in the presence of a test compound.

A control dose response curve is produced in isolated segments of guinea pig ileum mounted in an automated apparatus with six concentrations of prostaglandin E₂. A solution or suspension of test compound is substituted for the control bathing solution and is incubated for thirty minutes. An additional prostaglandin E₂ dose response curve is then performed in the presence of the test compound. A dose ratio is calculated from the EC₅₀ values obtained from duplicate replications on each concentration of the test compound. A concentration of test compound is judged to be active if it produces a dose ratio significantly greater than that obtained in a series of blank treatments.

A dose ratio of EC₅₀ doses was calculated from the results of each test in a manner known by those of skill in the art, and described above. A test compound was determined to be "active" if the initial concentration used yielded at least a two-fold shift (dose ratio greater than or equal to 2) in the dose response curve for prostaglandin E₂.

The results of this prostaglandin antagonism assay are also presented in Table 1 hereinbelow. The compounds of the present invention which were tested in this assay, and for which results are presented in Table 1, correspond to the particular examples specified in Table 1.

TABLE 1

| | Data Generated from the Assays | |
|---|---|---|
| Example Number | WRITHING ASSAY Number Out of Ten or ED₅₀ Dose I.G. | PGE ANTAGONISM IN GUINEA PIG ILEUM Dose Ratio |
| Example 2 | 6/10 | 5.0 ± 2.6 |
| Example 4 | 4/10 | 153 ± 74 |
| Example 6 | 6/10 | 6.8 ± 4.5 |
| Example 7 | 9.7 | 22 ± 5 |
| Example 8 | 6/10 | 1.9 ± 0.9 |

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having a structure:

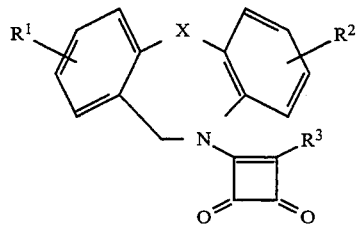

or a pharmaceutically-acceptable salt thereof, wherein:

X is oxygen, sulfur,

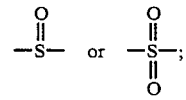

$R^1$ is hydrogen or halogen;
$R^2$ is hydrogen or halogen;
$R^3$ is $-NR^4R^5$, alkoxy,

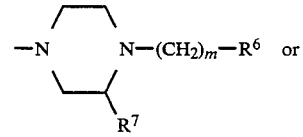

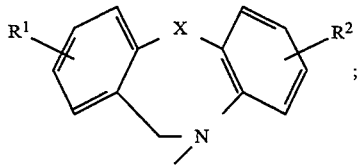

$R^4$ is hydrogen or alkyl;
$R^5$ is alkyl, alkylene-$NR^4R^4$ or alkylaryl;
$R^6$ is $-CH_3$ or aryl;
$R^7$ is hydrogen or

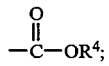

and
m is an integer of from 0 to 5.

2. A compound of claim 1 wherein X is oxygen.
3. A compound of claim 2 wherein $R^1$ is hydrogen.
4. A compound of claim 3 wherein $R^2$ is halogen.
5. A compound of claim 4 wherein $R^3$ is

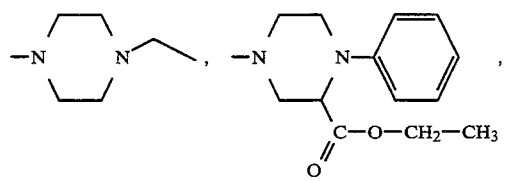

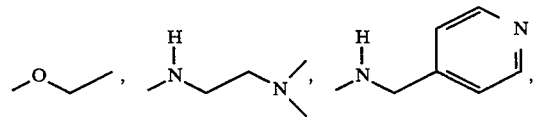

or 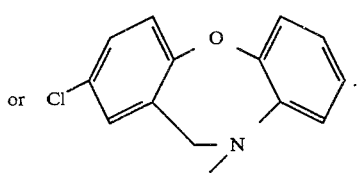.

6. A compound of claim 1, wherein the compound is:

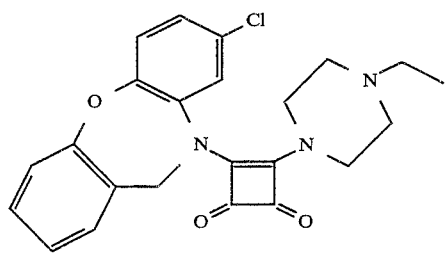

7. A compound of claim 1, wherein the compound is:

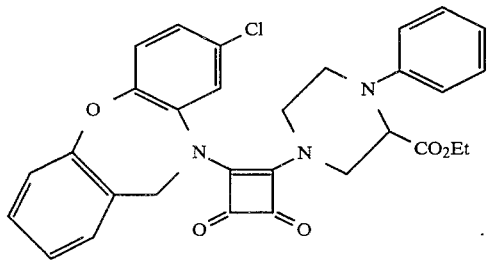

8. A compound of claim 1, wherein the compound is:

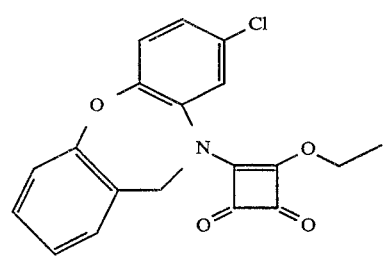

9. A compound of claim 1, wherein the compound is:

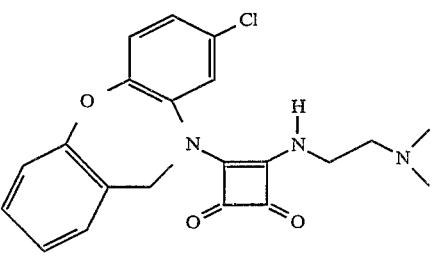

10. A compound of claim 1, wherein the compound is:

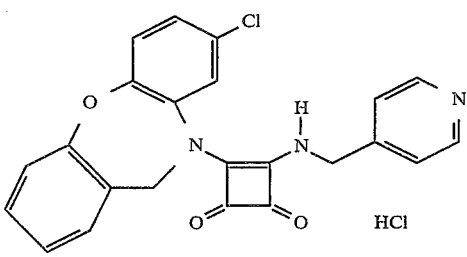

11. A compound of claim 1, wherein the compound is:

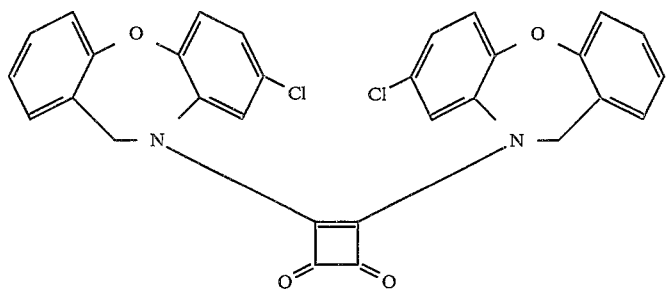

12. A pharmaceutical composition comprising a pharmaceutically-acceptable carrier and a therapeutically-effective amount of a compound having a structure:

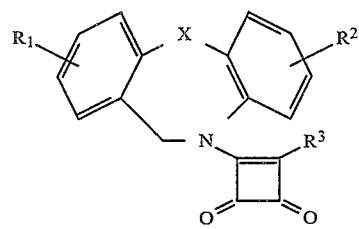

or a pharmaceutically-acceptable salt thereof, wherein:
X is oxygen, sulfur,

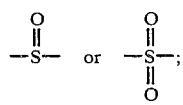

$R^1$ is hydrogen or halogen;
$R^2$ is hydrogen or halogen;
$R^3$ is —$NR^4R^5$, alkoxy,

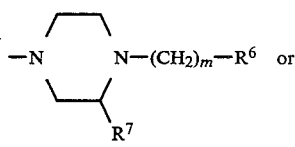

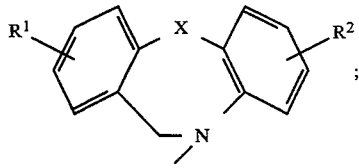

R⁴ is hydrogen or alkyl;
R⁵ is alkyl, alkylene-NR⁴R⁴ or alkylaryl;
R⁶ is —CH₃ or aryl;
R⁷ is hydrogen or

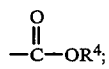

and m is an integer of from 0 to 5.

13. The pharmaceutical composition of claim 12 wherein the compound is:
3-(8-Chlorodibenz[b, f][1,4 ]oxazepin-10(11H)-yl)-4-(4-ethyl-1-1-piperazinyl)-3-cyclobutene-1,2-dione, monohydrochloride;
Ethyl 4-[2-(8-chlorodibenz[b,f][1,4 ]oxazepin-10(11H)-yl)-3,4-dioxo-1-cyclobuten-1-yl]-1-phenyl-2-piperazinecarboxylate;
3-(8-Chloro-dibenz[b,f][1,4]oxazepin-10(11H)-yl)-4-ethoxy-3-cyclobutene-1,2-dione;
3-(8-Chlorodibenz[b,f][1,4]oxazepin-10(11H)-yl)-4-[[2-(dimethylamino)ethyl]amino]-3-cyclobutene-1,2-dione, hydrochloride;
3-(8-Chlorodibenz[b,f][1,4]oxazepin-10(11H)-yl)-4-[(4-pyridinylmethyl)amino]-3-cyclobutene-1,2-dione, hydrochloride;
or
3,4-bis[8-chlorodibenz[b,f][1,4]oxazepin-10(11H)-yl-3-cyclobutene-1,2-dione.

14. A method for treating pain in an animal comprising administering to said animal a therapeutically-effective amount of a compound having a structure:

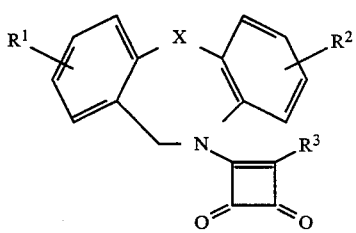

or a pharmaceutically-acceptable salt thereof, wherein:
X is oxygen, sulfur,

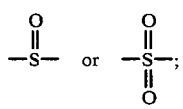

R¹ is hydrogen or halogen;
R² is hydrogen or halogen;
R³ is —NR⁴R⁴ alkoxy,

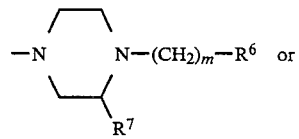

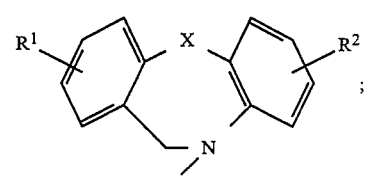

R⁴ is hydrogen or alkyl;
R⁵ is alkyl, alkylene-NR⁴R⁴ or alkylaryl;
R⁶ is —CH₃ or aryl;
R⁷ is hydrogen or

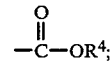

and m is an integer of from 0 to 5.

15. The method of claim 14 wherein the compound is:
3-(8-Chlorodibenz[b,f][1,4]oxazepin-10(11H) -yl)-4-(4-ethyl-1-1-piperazinyl)-3-cyclobutene-1,2-dione, monohydrochloride;
Ethyl 4-[2-(8-chlorodibenz[b,f][1,4 ]oxazepin-10(11H)-yl)-3,4-dioxo-1-cyclobuten-1-yl]-1-phenyl-2-piperazinecarboxylate;
3-(8-Chloro-dibenz[b,f][1,4]oxazepin-10(11H)-yl)-4-ethoxy-3-cyclobutene-1,2-dione;
3-(8-Chlorodibenz[b,f][1,4]oxazepin-10 (11H)-yl )-4-[[2-(dimethylamino)ethyl]amino]-3-cyclobutene-1,2-dione, hydrochloride;
3-(8-Chlorodibenz[b,f][1,4]oxazepin-10(11H)-yl)-4-[(4-pyridinylmethyl)amino]-3-cyclobutene-1,2-dione, hydrochloride;
or
3,4-bis[8-chlorodibenz[b,f][1,4]oxazepin-10(11H)-yl-3-cyclobutene-1,2-dione.

16. A method for treating diseases responsive to prostaglandin-E₂ antagonists in an animal comprising administering to said animal a therapeutically-effective amount of a compound having a structure:

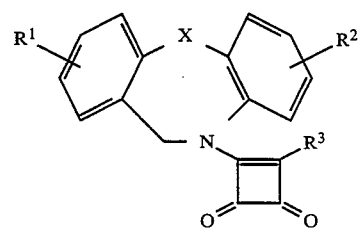

or a pharmaceutically-acceptable salt thereof, wherein:
X is oxygen, sulfur,

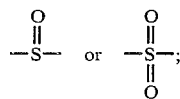

R[1] is hydrogen or halogen;
R[2] is hydrogen or halogen;
R[3] is —NR[4]R[5], alkoxy,

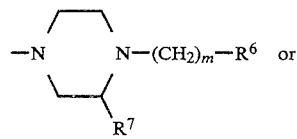

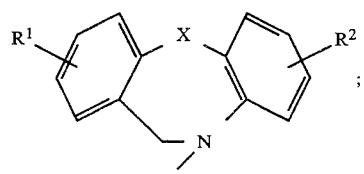

R[4] is hydrogen or alkyl;
R[5] is alkyl, alkylene-NR[4]R[4] or alkylaryl;

R[6] is —CH$_3$ or aryl;
R[7] is hydrogen or

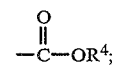

and
m is an integer of from 0 to 5.

17. The method of claim 16 wherein the compound is:
3-(8-Chlorodibenz[b,f][1,4]oxazepin-10(11H)-yl)-4-(4-ethyl-1-piperazinyl)-3-cyclobutene-1,2-dione, monohydrochloride;
Ethyl 4-[2-(8-chlorodibenz[b,f][1,4]oxazepin-10(11H)-yl)-3,4-dioxo-1-cyclobuten-1-yl]-1-phenyl-2-piperazinecarboxylate;
3-(8-Chloro-dibenz [b,f][1,4]oxazepin-10(11H)-yl)-4-ethoxy-3-cyclobutene-1,2-dione;
3-(8-Chlorodibenz[b,f][1,4]oxazepin-10(11H)-yl)-4-[[2-(dimethylamino)ethyl]amino]-3-cyclobutene-1,2-dione, hydrochloride;
3-(8-Chlorodibenz[b,f][1,4]oxazepin-10(11H)-yl)-4-[(4-pyridinylmethyl)amino]-3-cyclobutene-1,2-dione, hydrochloride;
or
3,4-bis[8-chlorodibenz[b,f][1,4]oxazepin-10(11H)-yl-3-cyclobutene-1,2-dione.

* * * * *

UNITED STATES PATENT AND TRADEMARK OFFICE
CERTIFICATE OF CORRECTION

PATENT NO. : 5,354,746          Page 1 of 2
DATED      : October 11, 1994
INVENTOR(S): Chandrakumar, et al.

It is certified that error appears in the above-indentified patent and that said Letters Patent is hereby corrected as shown below:

Column 1, line 46, reading "[1,41" should read -- [1,4] --.

Column 1, line 51, reading "[1,41" should read -- [1,4] --.

Column 1, line 55, reading "[1,41" should read -- [1,4] --.

Column 1, line 57, reading "8chlorodibenz" should read -- 8-chlorodibenz --. And "[1, 41" should read --[1,4]--.

Column 4, line 64, reading "(-CH$_3$OH)" should read --(CH$_3$OH)--.

Column 5, line 1, reading "as Used" should read -- as used --.

Column 7, line 20, reading "J. Pharm. Sci," should read -- J. Pharm. Sci., --.

Column 8, line 17, reading "preparation" should read -- Preparation --.

Column 12, line 65, reading "oilsoluble" should read -- oil-soluble --.

Column 14, line 62, reading "bentonitc," should read -- bentonite, --.

Column 18, line 3, reading "10(!!H)" should read -- 10(11H) --.

Column 19, line 59, reading "5 psi" should read -- 5 psi. --.

Column 20, line 30, reading "C$_{30}$H$_{20}$ClN$_3$O$_5$" should read -- C$_{30}$H$_{26}$ClN$_3$O$_5$ --.

UNITED STATES PATENT AND TRADEMARK OFFICE
CERTIFICATE OF CORRECTION

PATENT NO. : 5,354,746
DATED : October 11, 1994
INVENTOR(S) : Chandrakumar, et al.

It is certified that error appears in the above-indentified patent and that said Letters Patent is hereby corrected as shown below:

Column 29, line 45, reading "-yl-3-" should read -- -yl]-3- --.

Column 30, line 4, reading "-$NR^4R^4$" should read -- -$NR^4R^5$ --.

Column 30, line 34, reading "(4-ethyl-1-1-" should read -- (4-ethyl-1- --.

Column 30, line 49, reading "-yl-3-" should read -- -yl]-3- --.

Column 32, line 26, reading "-yl-3-" should read -- -yl]-3- --.

Signed and Sealed this

Fifth Day of September, 1995

BRUCE LEHMAN

*Attest:*

*Attesting Officer*       *Commissioner of Patents and Trademarks*